(12) United States Patent
Bakhtyari-Nejad-Esfahani

(10) Patent No.: US 8,758,300 B2
(45) Date of Patent: Jun. 24, 2014

(54) IMPROVEMENTS RELATING TO THE INSERTION OF A MEDICAL NEEDLE

(75) Inventor: Arash Bakhtyari-Nejad-Esfahani, Nottinghamshire (GB)

(73) Assignee: Olberon Medical Innovation SAS, Loos (FR)

( * ) Notice: Subject to any disclaimer, the term of this patent is extended or adjusted under 35 U.S.C. 154(b) by 950 days.

(21) Appl. No.: 12/295,268

(22) PCT Filed: Mar. 29, 2007

(86) PCT No.: PCT/GB2007/050171
§ 371 (c)(1),
(2), (4) Date: Sep. 29, 2008

(87) PCT Pub. No.: WO2007/110675
PCT Pub. Date: Oct. 4, 2007

(65) Prior Publication Data
US 2009/0259143 A1    Oct. 15, 2009

(30) Foreign Application Priority Data
Mar. 29, 2006 (GB) .................................. 0606287.1

(51) Int. Cl.
*A61M 5/00* (2006.01)
(52) U.S. Cl.
USPC .......................................... 604/117; 604/511
(58) Field of Classification Search
USPC ......... 604/510, 511, 513, 115, 116, 117, 162, 604/174, 177, 240, 268, 35, 36; 600/577, 600/578
See application file for complete search history.

(56) References Cited

U.S. PATENT DOCUMENTS

| 2,198,666 | A | * | 4/1940 | Gruskin | ........................ 604/117 |
| 2,457,464 | A | * | 12/1948 | Grose | ........................... 604/117 |
| 3,324,854 | A | | 6/1967 | Weese | |
| 4,299,219 | A | | 11/1981 | Norris, Jr. | |
| 4,332,248 | A | | 6/1982 | DeVitis | |
| 4,393,870 | A | | 7/1983 | Wagner | |
| 4,576,168 | A | | 3/1986 | Jalowayski | |
| 4,586,924 | A | | 5/1986 | Lanning | |
| 4,619,248 | A | | 10/1986 | Walsh | |
| 4,638,792 | A | | 1/1987 | Burgin | |
| 4,664,651 | A | | 5/1987 | Weinshenker et al. | |
| 5,320,607 | A | | 6/1994 | Ishibashi | |
| 5,364,362 | A | | 11/1994 | Schulz | |
| 5,415,647 | A | | 5/1995 | Pisarik | |

(Continued)

FOREIGN PATENT DOCUMENTS

DE    19620314 A1    11/1997
EP    1944051    7/2008

(Continued)

*Primary Examiner* — Kami A Bosworth
*Assistant Examiner* — Glen Janson
(74) *Attorney, Agent, or Firm* — Knobbe Martens Olson & Bear LLP

(57) ABSTRACT

A device (10) for at least partially inserting a needle (16) into the body of a patient is disclosed. The device (10) comprises a connector adapted for attachment to a needle (16), and a guard member (18) having a guide surface adapted to rest against a surface of the skin. The connector is adapted to set an attached needle (16) with a fixed position relative to the guard member (18), such that movement of the guide surface along the surface of the skin at least partially inserts the needle (16) into the body.

29 Claims, 4 Drawing Sheets

(56) References Cited

U.S. PATENT DOCUMENTS

| | | | |
|---|---|---|---|
| 5,478,315 | A | 12/1995 | Brothers et al. |
| 5,680,872 | A | 10/1997 | Sesekura et al. |
| 5,984,890 | A | 11/1999 | Gast et al. |
| 6,254,580 | B1 | 7/2001 | Svedman |
| 6,394,984 | B1 | 5/2002 | Hill |
| 6,814,737 | B2 | 11/2004 | Cauthen |
| 2001/0044606 | A1 | 11/2001 | Inkpen et al. |
| 2002/0049391 | A1* | 4/2002 | Kuracina et al. ............... 600/576 |
| 2002/0077599 | A1* | 6/2002 | Wojcik ........................... 604/162 |
| 2003/0181874 | A1* | 9/2003 | Bressler et al. ................ 604/263 |
| 2004/0199140 | A1 | 10/2004 | Rue et al. |
| 2010/0049241 | A1 | 2/2010 | Persson |
| 2010/0137799 | A1 | 6/2010 | Imai |

FOREIGN PATENT DOCUMENTS

| | | |
|---|---|---|
| FR | 542914 A | 8/1922 |
| FR | 542914 A1 | 8/1922 |
| FR | 2 612 401 A1 | 9/1988 |
| FR | 2612401 A | 9/1988 |
| FR | 2612401 A1 | 9/1988 |
| FR | 2698778 A1 | 6/1994 |
| FR | 2698778 A1 | 6/1994 |
| GB | 553728 A | 3/1946 |
| GB | 2 301 035 A | 11/1996 |
| GB | 2301035 | 11/1996 |
| GB | 2438518 | 11/2007 |
| RU | 2109525 C1 | 4/1998 |
| WO | WO 95/07722 | 3/1995 |
| WO | WO9507722 A1 | 3/1995 |
| WO | WO 98/25512 A1 | 6/1998 |
| WO | WO0134019 A | 5/2001 |
| WO | WO02/100457 A | 12/2002 |
| WO | WO 02/100457 A2 | 12/2002 |
| WO | WO 2006/007629 | 1/2006 |
| WO | WO2006/054280 | 5/2006 |
| WO | WO2006054280 | 5/2006 |

* cited by examiner

IMPROVEMENTS RELATING TO THE INSERTION OF A MEDICAL NEEDLE

CROSS REFERENCE TO RELATED APPLICATIONS

This application claims the benefit and priority to and is a U.S. National Phase of PCT International Application Number PCT/GB2007/050171, filed on Mar. 29, 2007. This application claims the benefit and priority to United Kingdom Application No. GB 0606287.1 filed on Mar. 29, 2006. The disclosures of the above-referenced applications are hereby expressly incorporated by reference in their entirety.

The present invention relates to devices and methods for at least partially inserting a medical needle, such as a hypodermic needle, into the body of a patient.

A hypodermic needle is a hollow needle commonly used with a syringe to inject substances into the body of a patient. They may also be used to take liquid samples from the body of a patient, for example taking blood from a vein in venipuncture.

Syringes having hypodermic needles attached are often used for delivering substances to a patient. These substances may be, for example, vaccines or drugs (for example, local anaesthetics). For example, an injection can be given directly into the bloodstream (intravenously), into muscle (intra-muscularly) or into subcutaneous tissue (subcutaneously). In certain cases, these substances need to be delivered into the superficial layer of skin. This is known as an intradermal injection.

Currently, small volumes (for example, 50-100 µl) are delivered into the superficial layer of skin using a conventional (but small volume, for example 1 ml) syringe. The person delivering the injection must hold the syringe at an angle of about 15° to the skin and at the same time provide controlled entry of the substance into the superficial layer of skin.

The use of a conventional syringe to deliver an intradermal injection can be very difficult due to the shallow angle required for the hypodermic needle with respect to the skin and the need for a very controlled penetration of the needle into the skin. This requires a needle tip to the inserted for about 1 to 2 mm and to a depth of about 1 mm. The success of this type of injection is dependent upon the skill of the person delivering the injection.

Another way of delivering substances intradermally has been developed, This involves needle-free injection technology in which liquid substances are forced at high speed through a tiny orifice held against the skin. The diameter of the orifice is smaller than the diameter of a human hair, which creates a stream of high pressure fluid that penetrates the skin without using a needle.

Although it has been suggested that this system could be used to carry out intradermal injections, this technology is not reproducible in terms of depth placement of the injection. This is because skin thickness and resistance to the fired jet of injection will vary from one patient to another. This needle-free technology is also complex and expensive.

A device that addresses one or more of the above problems is desirable.

According to a first aspect of the invention, there is provided a device for at least partially inserting a needle into the body of a patient, the device comprising a connector adapted for attachment to a needle, and a guard member having a guide surface adapted to rest against a surface of the skin, the connector being adapted to set an attached needle with a fixed position relative to the guard member, such that movement of the guide surface along the surface of the skin at least partially inserts the needle into the body.

The device according to the invention is advantageous principally because the guard member facilitates insertion of the needle into the body, and reduces the risk of an inaccurate insertion that might result in failure of the particular medical procedure being performed. Furthermore, the guard member may be adapted such that the needle is inserted a prescribed distance, and/or at a prescribed angle, into the body.

The needle may be permanently connected to the device, so that the needle forms an integral part of the device. For example, the device could be a single use device for delivering a substance to a patient.

The device is preferably arranged so that the guide surface maintains contact with the surface of the skin at all times during insertion of the needle. In particular, the device is preferably arranged to enable a user to grip the device and slide the guide surface along the surface of the skin. Furthermore, the device is preferably arranged so that the entire extent of the guide surface maintains contact with the surface of the skin during insertion of the needle, and hence the angle of the needle relative to the surface of the skin is constant. Most preferably, the connector is adapted to set the attached needle at an angle, other than perpendicular, relative to the guide surface of the guard member, such that movement of the guide surface along the surface of the skin in the direction in which the needle is inclined at least partially inserts the needle into the body.

The device is preferably arranged such that the guide surface may be located against a surface of the skin, without the tip of the needle being inserted into the skin. Subsequent movement of the guide surface along the surface of the skin then preferably inserts the tip of the needle into the body. In particular, the device may be arranged such that the needle projects beyond the plane of the guide surface, but does not puncture the skin when the guide surface is located against the surface of the skin. For instance, the needle may be resiliently deformed by the surface of the skin to a position substantially level with the plane of the guide surface. However, in presently preferred embodiments, the tip of the needle is substantially aligned with the plane of the guide surface, or slightly withdrawn relative to the plane of the guide surface. In this case, the needle projects beyond an end surface of the guard member, rather than beyond the guide surface.

Where the tip of the needle needs to be inserted into the body at a particular angle, the connector is preferably arranged to set an attached needle at a prescribed angle to the guide surface of the guard member. This ensures that a needle is inserted at a desired angle relative to the surface of the skin. In particular, where the device is intended for carrying out intradermal injections, the prescribed angle is preferably between approximately 5° and approximately 20°.

In a preferred embodiment, it is approximately 15°.

Where the tip of the needle needs to be inserted into the body a prescribed distance, the guard member is preferably able to block penetration into the body by more than a given amount of a needle attached to the connector. This ensures that a needle is inserted to the desired depth within the body. In particular, the device is preferably adapted so that only that portion of the needle that projects beyond the guide surface or end surface of the guard member is able to be inserted into the body. In a preferred embodiment, the guard member is able to block penetration of more than 1-2 mm. This arrangement is particularly suitable for intradermal injections.

The guide surface may be adapted such that whilst the guide surface is located against a surface of the skin, in use, the orientation of the device relative to that surface is constant. In particular, the guide surface may be substantially flat, or may comprise two or more edges that are arranged in the same plane. This facilitates movement of the guide surface along the surface of the skin, and also enables the guard member to act more reliably in setting the needle at the correct angle relative to the surface of the skin. The end surface of the guard member preferably extends from one end of the guide surface, at an angle thereto. Most preferably, the end surface of the guard member is rounded in form.

The device may comprise a plurality of guard members that define the guide surface. The one or more guard members are preferably arranged so that only a minor portion of the needle attached to the connector projects beyond the guard member(s). In presently preferred embodiments, the device is provided with two guard members that are situated to each side of the needle. In this arrangement, the guard members include juxtaposed lower edges that together define the guide surface of the guard members. Alternatively, the guard member may comprise a plate with an exterior surface that defines the guide surface. In this arrangement, the plate may include an aperture through which the tip of the needle projects, or else the tip of the needle may project beyond an end surface of the plate.

The device according to the invention may be a syringe for delivering substances to a patient. In particular, the present invention is particularly advantageous where the device is a syringe adapted for carrying out intradermal injections. Where the device is a syringe, the device preferably comprises a barrel and a connector to which a hypodermic needle can be attached for giving injections. The guard member preferably comprises one or more projections extending from the barrel of the syringe, the one or more projections being arranged with respect to the connector such that the one or more projections extend in substantially the same direction as a needle attached to the syringe. Furthermore, the barrel and the needle connector are preferably arranged such that when a needle is attached to the syringe, the longitudinal axis of the barrel and the longitudinal axis of the needle are at an angle to one another. The angle is preferably in the range of approximately 45° to approximately 165°, and preferably approximately 70° to approximately 165°. The angle is preferably approximately 120°. This arrangement means that the person giving the injection can hold the syringe at a natural angle, thereby facilitating the giving of the injection. The barrel of the syringe can be, for example, almost perpendicular to surface being injected, whereas the needle can be inserted at a shallow angle, for example an angle of around 15°.

Alternatively, the device according to the invention may be a holder adapted for inserting a hypodermic needle into the body of a patient in order to take liquid samples from that patient. In particular, the device may be adapted for inserting a hypodermic needle into a vein in order to take a sample of blood from a patient. In this case, the hypodermic needle may be readily detachable from the connector of the holder, such that the hypodermic needle may be attached to a device for withdrawing a sample of blood once it has been inserted into the vein. Alternatively, the holder may itself be adapted for connection to a device for withdrawing a sample of blood through the hypodermic needle. In particular, the holder may be adapted for operable connection to an evacuated collection vessel, such as a Vacutainer®, such that a sample of blood is drawn through the hypodermic needle into the collection vessel by the reduced pressure within the collection vessel. In this case, the holder preferably includes means for opening a rupturable closure of the collection vessel on connection of the holder with the collection vessel. Such means preferably takes the form of a needle.

According to a further aspect of the invention, there is provided a method of at least partially inserting a needle into a body, the method comprising the steps of:

(a) providing a device as described above;

(b) locating the guide surface against a surface of the skin; and (c) moving the guide surface along the surface of the skin, such that the needle is at least partially inserted into the body.

This method facilitates insertion of the needle into the body, and reduces the risk of an inaccurate insertion that might result in failure of the particular medical procedure being performed. Furthermore, the guard member may be adapted such that the needle is inserted a prescribed distance, and/or at a prescribed angle, into the body.

The guide surface preferably maintains contact with the surface of the skin at all times during insertion of the needle. In particular, the user preferably grips the device and slides the guide surface along the surface of the skin. Furthermore, the entire extent of the guide surface preferably maintains contact with the surface of the skin during insertion, such that the angle of the needle relative to the surface of the skin is constant.

Where the connector is adapted to set the attached needle at an angle, other than perpendicular, relative to the guide surface of the guard member, the guide surface is preferably moved along the surface of the skin in the direction in which the needle is inclined, such that the needle is at least partially inserted into the body.

The device may be arranged such that the needle projects beyond the plane of the guide surface, but does not puncture the skin when the guide surface is located against the surface of the skin. In particular, the needle may be resiliently deformed by the surface of the skin to a position substantially level with the plane of the guide surface. However, in presently preferred embodiments, the tip of the needle is substantially aligned with the plane of the guide surface, or slightly withdrawn relative to the plane of the guide surface. In this case, the needle projects beyond an end surface of the guard member, rather than beyond the guide surface. Where the tip of the needle is substantially aligned with the plane of the guide surface, the guide surface is preferably located against the surface of the skin and moved along that surface, such that the needle catches on the surface of the skin, and is then at least partially inserted into a portion of the skin adjacent to the end surface of the guard member. Where the tip of the needle is slightly withdrawn relative to the level of the guide surface, the guide surface is preferably located against the surface of the skin and moved along that surface, such that the needle is at least partially inserted into a portion of the skin that is raised, in use, relative to the guide surface. The raised portion of the skin may be formed by applying pressure to the device towards the surface of the skin, so that the guide surface depresses the surface of the skin with which it is in contact. Alternatively, there may be sufficient friction between the guide surface and the surface of the skin to cause a portion of the skin to be raised, adjacent to the end surface of the guard member, into which the needle is inserted.

A preferred embodiment of the present invention is described below, by way of example only, and with reference to the accompanying drawings, in which.

Figure 1:
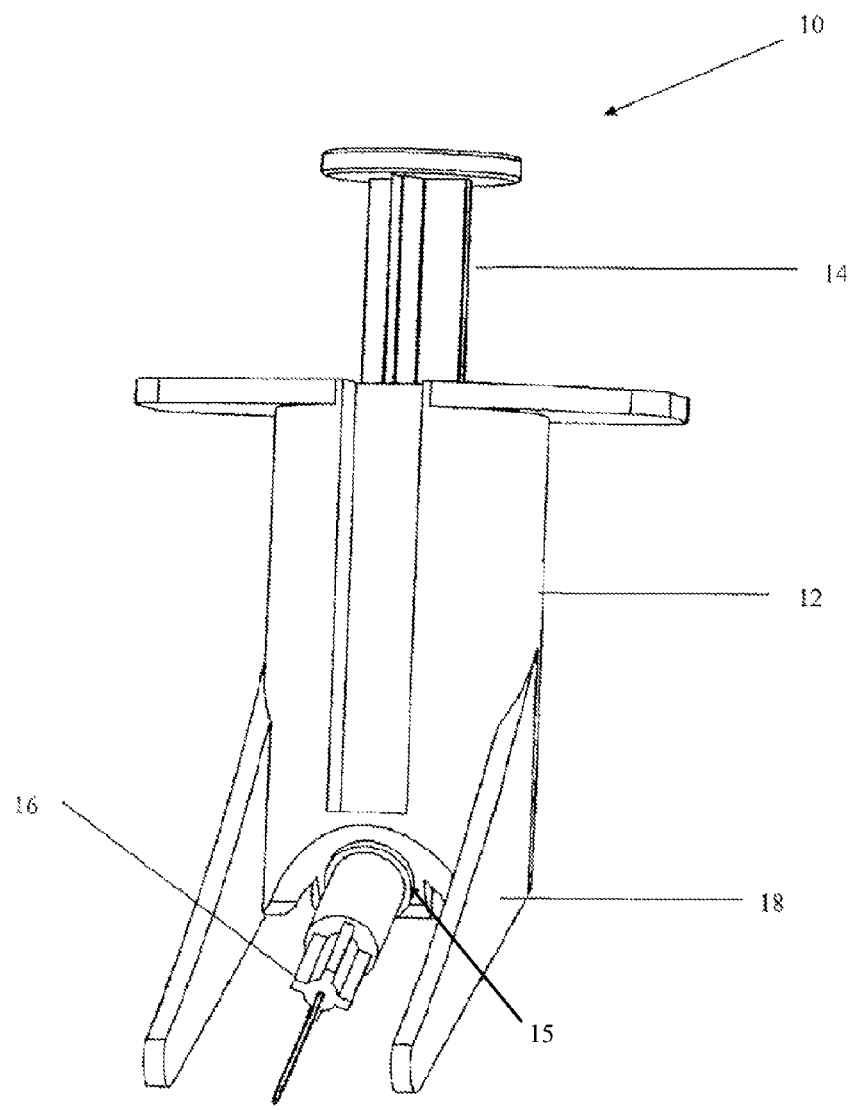
FIG. 1 shows a perspective view of a syringe according to the invention.
Figure 2:
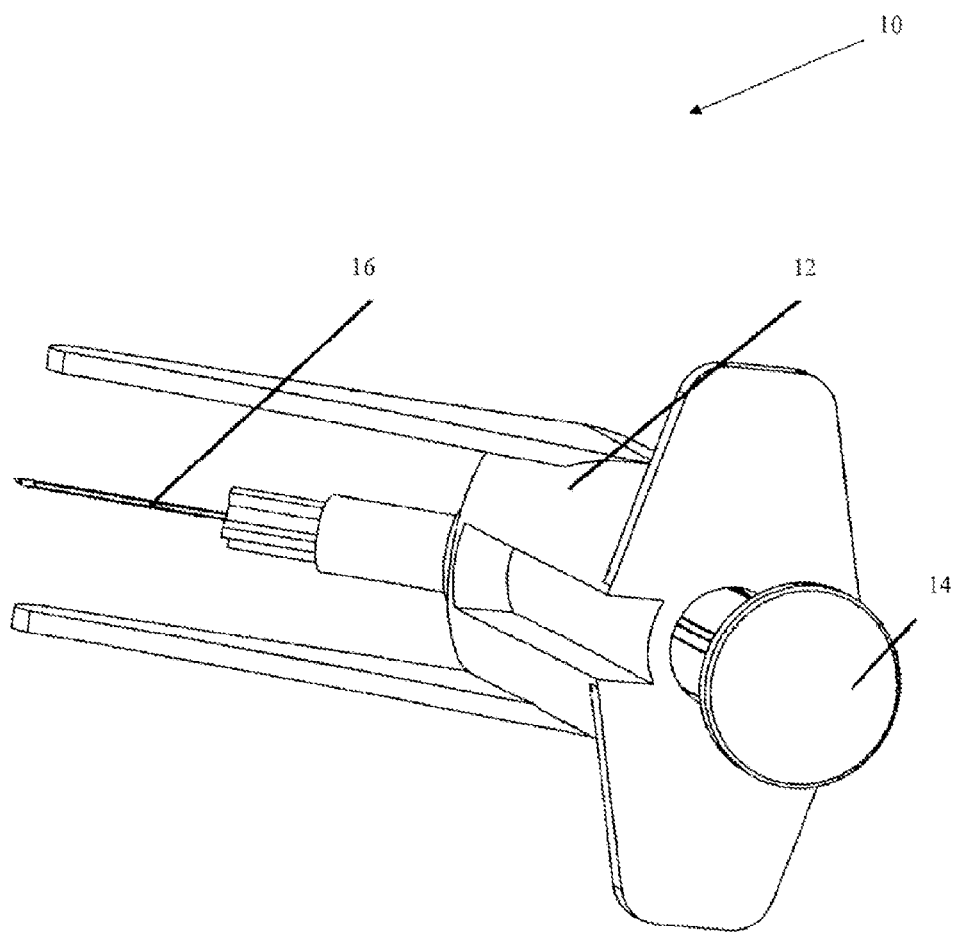
FIG. 2 shows a top view of the syringe of FIG. 1.
Figure 3:
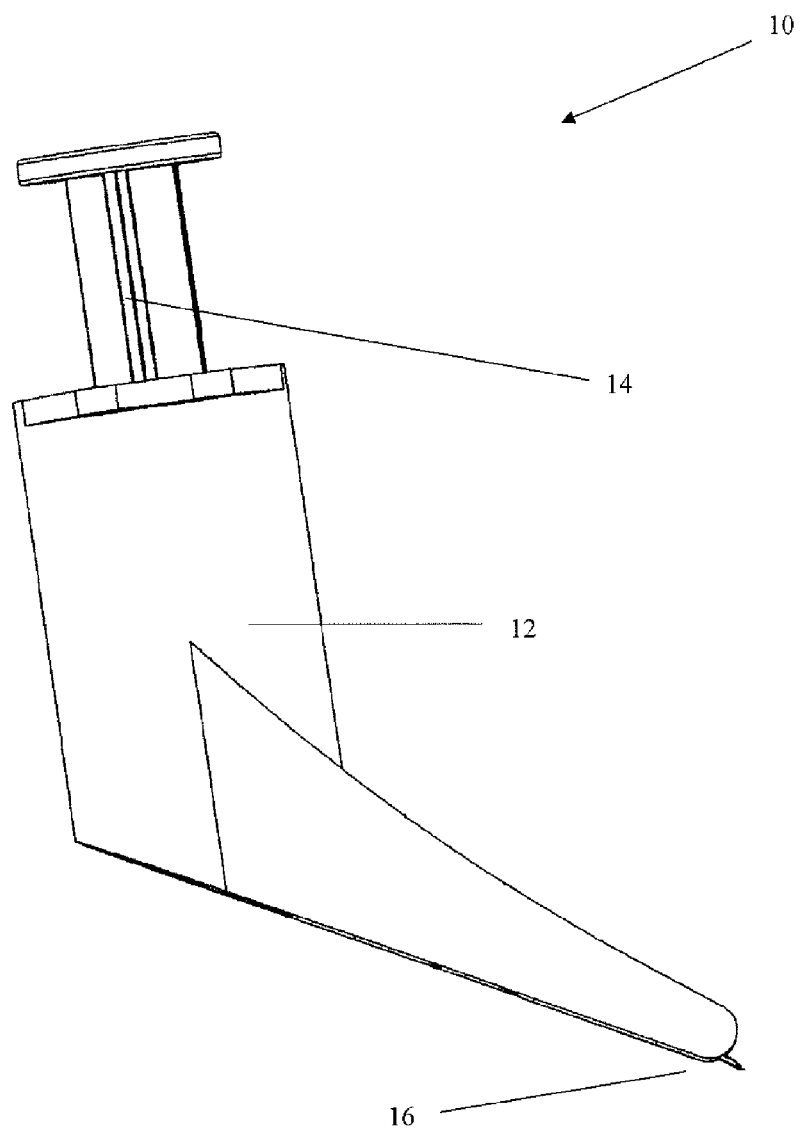
FIG. 3 shows a side view of the syringe of FIG. 1.

Referring to FIGS. 1 to 3, a preferred embodiment of a syringe 10 includes a barrel 12 for holding a substance to be injected prior to an injection. A plunger 14 is able to move within barrel 12 in a conventional manner. The syringe 10 has a connector 15 to which a needle 16 is attached. This connection may be permanent or detachable. The connector 15 and the barrel 12 are arranged such that when a needle 16 is attached, the longitudinal axes of needle and the barrel are at an angle of approximately 120° with respect to one another. This angle facilitates manipulation of the syringe 10 by the person giving the injection and enables them to have more control over the syringe 10. This is because, whilst giving the injection, the barrel of the syringe can be held at a more natural angle.

Attached to each side of the barrel 12, at its lower, delivery, end, is a needle guard 18. Each needle guard 18 has a guide edge or surface that extends at angle from the barrel 12, in substantially the same direction as an attached needle 16. The preferred syringe is intended for use with a needle having a length of 16 mm and a diameter of 0.5 mm. As can be seen in FIGS. 2 and 3, the length of the needle guards 18 is such that an attached needle 16 extends beyond the needle guards 18 by approximately 1 mm, ie by the amount by which the needle 16 should penetrate the skin. The needle guards 18 thus limit the depth of penetration of the skin by the needle 16. The needle guards 18 also allow controlled and reproducible needle placement at an appropriate depth and at an appropriate angle in the skin. In addition, the needle guards 18 are arranged such that the tip of the attached needle 16 is substantially aligned with the guide surface of the needle guards 18.

A projecting portion of the needle 16 extends outwardly from the connector 15 to the needle tip. Each of the needle guards 18 include a lower edge and an upper edge. At least one needle guard 18 is situated to each side of the needle 16 and extends upward from the lower edge such that the entire upper edge of each needle guard 18 is above the projecting portion of the needle.

In the preferred embodiment each needle guard 18 is a triangular projection. The needle guard 18 has a flat base for resting on the skin thereby providing support for the needle 16 and syringe 10. The needle guards 18 are attached to the barrel 12 by the short edges of the triangles.

Figure 4:
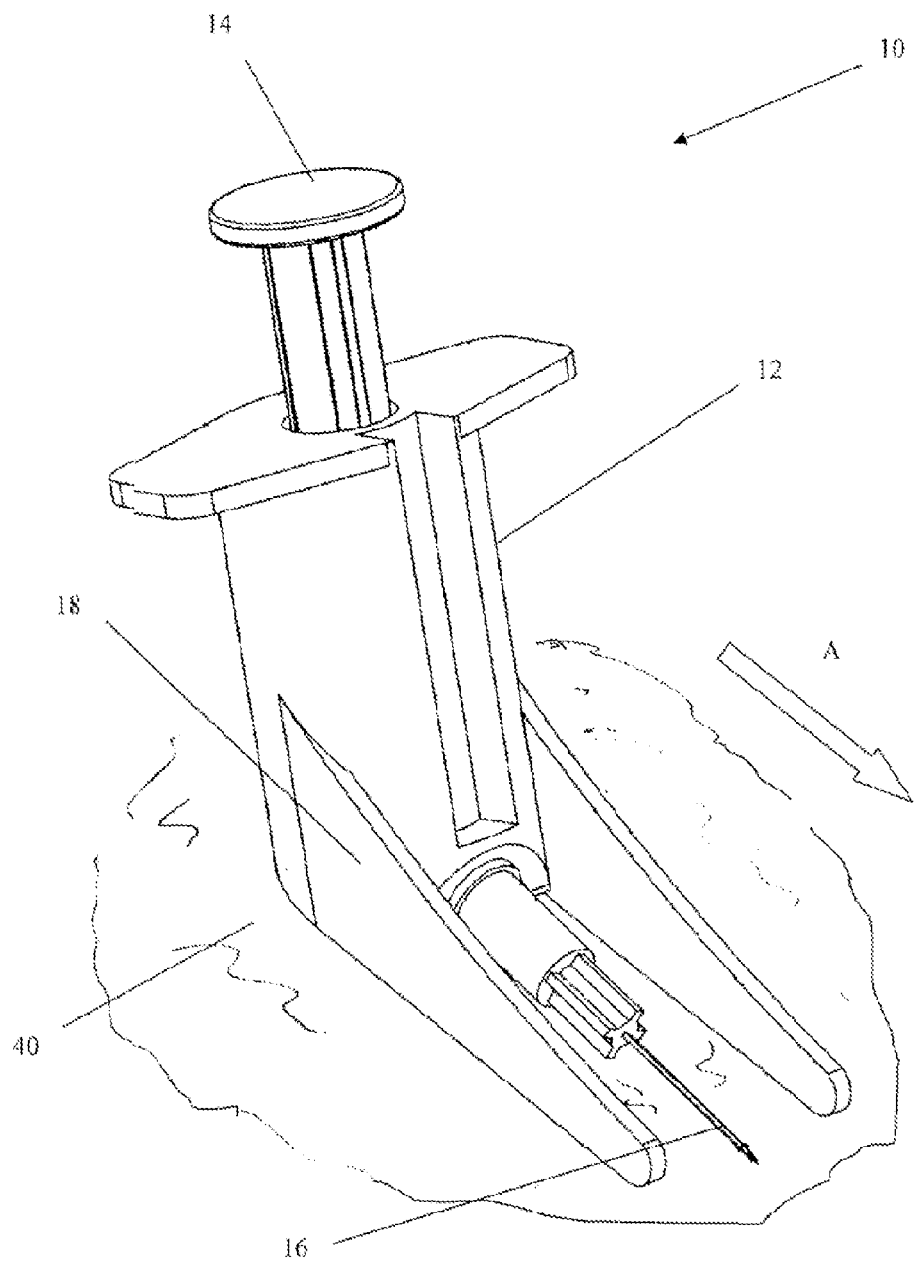
FIG. 4 shows a perspective view of the syringe of FIG. 1 in use.

FIG. 4 illustrates the syringe 10 in use. The person giving the injection rests the needle guard 18 of the syringe 10 on the skin 40 close to the injection site. The syringe is slid (illustrated by Arrow A) for a distance of 2 mm-3 mm across the skin 40. This causes the tip of the needle 16 to engage into the superficial layer of the skin 40 at the desired angle. Excessive depth penetration of the needle 16 into the skin 40 is avoided due to the presence of the needle guards 18. Once the needle has been correctly placed, the injection can be given by downward movement of the plunger 14 within the barrel 12 in the conventional manner.

There are various advantages to the above described embodiment.

It is envisaged that a number of vaccines (present and under development) are to be given through an intradermal injection. The above described syringe 10 is ideally suited for the delivery of such vaccines. Additionally, this syringe can be used to inject small amounts of local anaesthetic intradermally in a localised area of skin prior to placement of an intravenous cannula. Using this syringe 10, the placement of an intravenous cannula should be routinely less painful for a patient. An intradermal syringe 10 filled with local anaesthetic could be used for this purpose.

The provision of the needle guards 18 makes the giving of intradermal injections much easier, minimising the skill required for effective and consistent use. Needle guards 18 having a flat base as described provide improved support to the syringe 10, facilitating use of the syringe 10 by the person giving the injection. They also allow the syringe 10 to slide along the skin as the needle 16 is inserted. They also provide improved reproducibility of injection placement.

The extending of the needle by only 1 to 2 mm beyond the needle guards 18 allows precise yet superficial positioning of the needle tip in the skin. This enables an intradermal injection to be given within the correct layer of skin.

There are various modifications that could be made to the above described embodiment.

The needle guards 18 need not be the exact shape shown in the Figures. A skilled person would appreciate that other forms of guard could be suitable, For example, the needle guards 18 could be "L"-shaped. A single needle guard 18, or several needle guards 18 could be provided.

Needle guards 18 could even be useful in a syringe where the needle 16 and the barrel 12 are not at an angle to one another. However, as indicated above, the angle between the needle 16 and the barrel 12 renders the syringe easier to use.

The precise angle between the needle 16 and the barrel 12 need not be 120°. Any angle between the needle 16 and the barrel 12 will increase the space available between the barrel 12 and the skin 40 for manipulation of the syringe by the person giving the injection.

In a modification, where the syringe 10 may be used to deliver a local anaesthetic, for example, a glass vial prefilled with the anaesthetic and having a plunger could be used (due to the stability of anaesthetic in glass). The vial is fitted to the top of the syringe barrel 12. A double-ended angled needle 16 is permanently attached to the syringe 10. One end of the needle 16 pierces the vial, whereas the other is for injection into the skin.

Although this preferred embodiment has been described as an intradermal syringe 10 because of the particular problems associated with giving intradermal injections, the skilled person will appreciate that the described syringe could be modified in order to provide control over other depths and/or angles of injection. For example, a syringe having an appropriate guard could be particularly suitable for providing subcutaneous injections. A syringe 10 could include needle guards 18 that provide adjustable angles so that a single syringe could be used for different types of injections.

Depending on the type of injection being given, and the type of needle 16 being used, the syringe 10 may be of a different size to that described as preferred. The sizes of the needle guards 18 can also be altered as appropriate.

The invention claimed is:

1. A device for at least partially inserting a needle into a body of a patient, the device comprising a connector adapted for attachment to a needle such that a projecting portion of the needle extends outwardly from the connector to a needle tip, and a plurality of guard members, each of the guard members including a lower edge and an upper edge, at least one guard member being situated to each side of the needle and extending upward from the lower edge such that the entire upper edge of each guard member is above the projecting portion of the needle, wherein the lower edges are arranged such that the lower edges define spaced portions of a guide surface adapted to rest against a surface of the skin, the connector being adapted to set an attached needle with a fixed position relative to the guard members, wherein both the needle and the guard members extend forwardly of the connector and are arranged such that the guard members are able to block penetration into the body by more than a given amount of the needle attached to the connector, whereby movement of the guide surface along the surface of the skin partially inserts the needle into the body.

2. A device as claimed in claim 1, wherein the needle is permanently connected to the device, so that the needle forms an integral part of the device.

3. A device as claimed in claim 2, wherein the device is a single use device for delivering a substance to a patient.

4. A device as claimed in claim 1, wherein the device is arranged so that the guide surface maintains contact with the surface of the skin of the patient at all times during insertion of the needle.

5. A device as claimed in claim 4, wherein the device is arranged to enable a user to grip the device and slide the guide surface along the surface of the skin.

6. A device as claimed in claim 5, wherein the device is arranged so that the entire extent of the guide surface maintains contact with the surface of the skin during insertion of the needle, and hence the angle of the needle relative to the surface of the skin is constant.

7. A device as claimed in claim 1, wherein the connector is adapted to set the attached needle at an angle, other than perpendicular, relative to the guide surface of the guard members, such that movement of the guide surface along the surface of the skin in the direction in which the needle is inclined at least partially inserts the needle into the body.

8. A device as claimed in claim 1, wherein the device is arranged such that the guide surface may be located against a surface of the skin of the patient, without the tip of the needle being inserted into the skin.

9. A device as claimed in claim 8, wherein the needle projects beyond the plane of the guide surface, but does not puncture the skin when the guide surface is located against the surface of the skin.

10. A device as claimed in claim 8, wherein the tip of the needle is substantially aligned with the plane of the guide surface, or slightly withdrawn relative to the plane of the guide surface, and the needle projects beyond an end surface of the guard members.

11. A device as claimed in claim 1, wherein the connector is arranged to set an attached needle at a prescribed angle to the guide surface of the guard members.

12. A device as claimed in claim 1, wherein the device is adapted so that only that portion of the needle that projects beyond the guide surface or an end surface of the guard members is able to be inserted into the body.

13. A device as claimed in claim 1, wherein the guard members are able to block penetration of more than 1-2mm.

14. A device as claimed in claim 1, wherein the guide surface is adapted such that whilst the guide surface is located against a surface of the skin, in use, the orientation of the device relative to that surface is constant.

15. A device as claimed in claim 14, wherein the guide surface is substantially flat, or comprises two or more edges that are arranged in the same plane.

16. A device as claimed in claim 1, wherein the device is a syringe for delivering substances to a patient.

17. A device as claimed in claim 16, wherein the device is a syringe adapted for caffying out intradermal injections.

18. A device as claimed in claim 16, wherein the device comprises a barrel connected to the connector.

19. A device as claimed in claim 18, wherein the at least one guard member extends from the barrel of the syringe and extends in substantially the same direction as the needle.

20. A device as claimed in claim 18, wherein the barrel and the connector are arranged such that a longitudinal axis of the barrel and a longitudinal axis of the needle are at an angle to one another.

21. A device as claimed in claim 20, wherein the angle between the longitudinal axis of the barrel and the longitudinal axis of the needle is in the range of approximately 450 to approximately 165°.

22. A device as claimed in claim 1, wherein the device is a holder adapted for inserting a hypodermic needle into the body of a patient in order to take liquid samples from that patient.

23. A device as claimed in claim 22, wherein the device is adapted for inserting a hypodermic needle into a vein in order to take a sample of blood from a patient.

24. A method of at least partially inserting a needle into a body, the method comprising the steps of:
 (a) providing a device as claimed in claim 1;
 (b) locating the guide surface against a surface of the skin; and
 (c) moving the guide surface along the surface of the skin, such that the needle is at least partially inserted into the body.

25. A method as claimed in claim 24, wherein the guide surface maintains contact with the surface of the skin at all times during insertion of the needle.

26. A method as claimed in claim 25, wherein the user grips the device and slides the guide surface along the surface of the skin.

27. A method as claimed in claim 25, wherein the entire extent of the guide surface maintains contact with the surface of the skin during insertion, such that the angle of the needle relative to the surface of the skin is constant.

28. A device as claimed in claim 1, wherein the guard members partially enclose a portion of the needle.

29. A device as claimed in claim 1, wherein the guard members comprise triangular projections.

* * * * *